United States Patent
Eyal et al.

(10) Patent No.: US 9,833,187 B2
(45) Date of Patent: Dec. 5, 2017

(54) DETECTION, DIAGNOSIS AND MONITORING OF OSTEOPOROSIS BY A PHOTO-ACOUSTIC METHOD

(71) Applicant: Ramot at Tel-Aviv University Ltd., Tel-Aviv (IL)

(72) Inventors: Avishay Eyal, Givat Shmuel (IL); Idan Steinberg, Ramat-Gan (IL); Israel Gannot, Ramat-HaSharon (IL)

(73) Assignee: Ramot at Tel-Aviv University Ltd., Tel-Aviv (IL)

( * ) Notice: Subject to any disclaimer, the term of this patent is extended or adjusted under 35 U.S.C. 154(b) by 102 days.

(21) Appl. No.: 14/762,816

(22) PCT Filed: Jan. 30, 2014

(86) PCT No.: PCT/IL2014/050108
§ 371 (c)(1),
(2) Date: Jul. 23, 2015

(87) PCT Pub. No.: WO2014/118781
PCT Pub. Date: Aug. 7, 2014

(65) Prior Publication Data
US 2015/0359478 A1    Dec. 17, 2015

Related U.S. Application Data

(60) Provisional application No. 61/758,787, filed on Jan. 31, 2013.

(51) Int. Cl.
*A61B 5/05* (2006.01)
*A61B 5/00* (2006.01)
(Continued)

(52) U.S. Cl.
CPC .......... *A61B 5/4509* (2013.01); *A61B 5/0035* (2013.01); *A61B 5/0095* (2013.01);
(Continued)

(58) Field of Classification Search
CPC .......................... A61B 5/0095; A61B 5/0093
(Continued)

(56) References Cited

U.S. PATENT DOCUMENTS 4,543,486 A * 9/1985 Rose ...................... B23K 26/03
219/121.14
5,259,384 A   11/1993 Kaufman et al.
(Continued)

FOREIGN PATENT DOCUMENTS

| WO | WO 2013/064740 | * 5/2013 | ............... A61B 5/00 |
| WO | WO 2014/118781 | 8/2014 | |

OTHER PUBLICATIONS

International Search Report and the Written Opinion dated May 25, 2014 From the International Searching Authority Re. Application No. PCT/IL2014/050108.
(Continued)

*Primary Examiner* — James Kish

(57) ABSTRACT

Method for examining bone in vivo, comprises obtaining a laser beam; modulating the laser beam to insert therein photoacoustic frequencies including optical frequencies and acoustic frequencies, the acoustic frequencies being able to give rise to acoustic waves; directing the modulated beam at a bone to cause acoustic waves resulting from the beam to travel through the bone; analyzing received signals from the bone including signals resulting from the acoustic waves, to determine a mineral density and a bone quality for said bone, and thus obtain in-vivo data that can be of assistance to a doctor when diagnosing osteoporosis.

11 Claims, 12 Drawing Sheets
(5 of 12 Drawing Sheet(s) Filed in Color)

(51) Int. Cl.
*A61B 8/00* (2006.01)
*A61B 8/08* (2006.01)

(52) U.S. Cl.
CPC .......... *A61B 5/0097* (2013.01); *A61B 8/0875* (2013.01); *A61B 8/4483* (2013.01); *A61B 8/08* (2013.01)

(58) Field of Classification Search
USPC .......................................... 600/407, 437–472
See application file for complete search history.

(56) References Cited

U.S. PATENT DOCUMENTS

| | | | |
|---|---|---|---|
| 6,212,421 | B1 | 4/2001 | Vo-Dinh et al. |
| 8,930,145 | B2 * | 1/2015 | Li .................. A61B 5/0059 600/407 |
| 2003/0167002 | A1 | 9/2003 | Nagar et al. |
| 2008/0173093 | A1 | 7/2008 | Wang et al. |
| 2009/0143681 | A1 | 6/2009 | Jurvelin et al. |
| 2011/0092818 | A1 * | 4/2011 | Sarvazyan ......... A61B 8/0875 600/449 |
| 2012/0029829 | A1 * | 2/2012 | Li .................. A61B 5/0059 702/19 |
| 2014/0187954 | A1 * | 7/2014 | Fatemi ............. A61B 5/4509 600/449 |

OTHER PUBLICATIONS

Lashkari et al. "Combined Photoacoustic and Ultrasonic Diagnosis of Early Bone Loss and Density Variations", Proceedings of the SPIE: Photonic Therapeutics and Diagnostics VIII, 8207: 82076K-1-82076K-6, Feb. 9, 2012.

Zhao et al. "Photo-Acoustic Excitation and Detection of Guided Ultrasonic Waves in Bone Samples Covered by a Soft Coating Layer", Proceedings of the SPIE: Optics in Health Care and Biomedical Optics V, 8553: 85531E-1-85531E-8, Dec. 11, 2012.

Supplementary European Search Report and the European Search Opinion dated Aug. 19, 2016 From the European Patent Office Re. Application No. 14745801.2.

Maslov et al. "Photoacoustic Imaging of Biological Tissue With Intensity-Modulated Continuous-Wave Laser", Journal of Biomedical Optics, XP055029069, 13(2): 024006-1-024006-6, Published Online Apr. 14, 2008. p. 4, 1-h Col., Lines 4-9, Abstract.

* cited by examiner

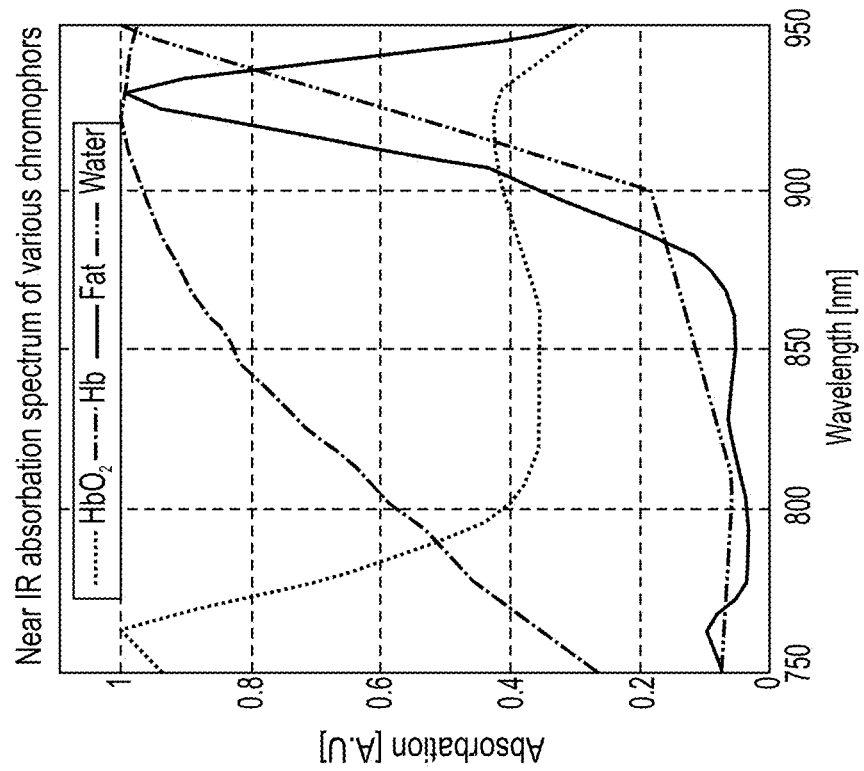
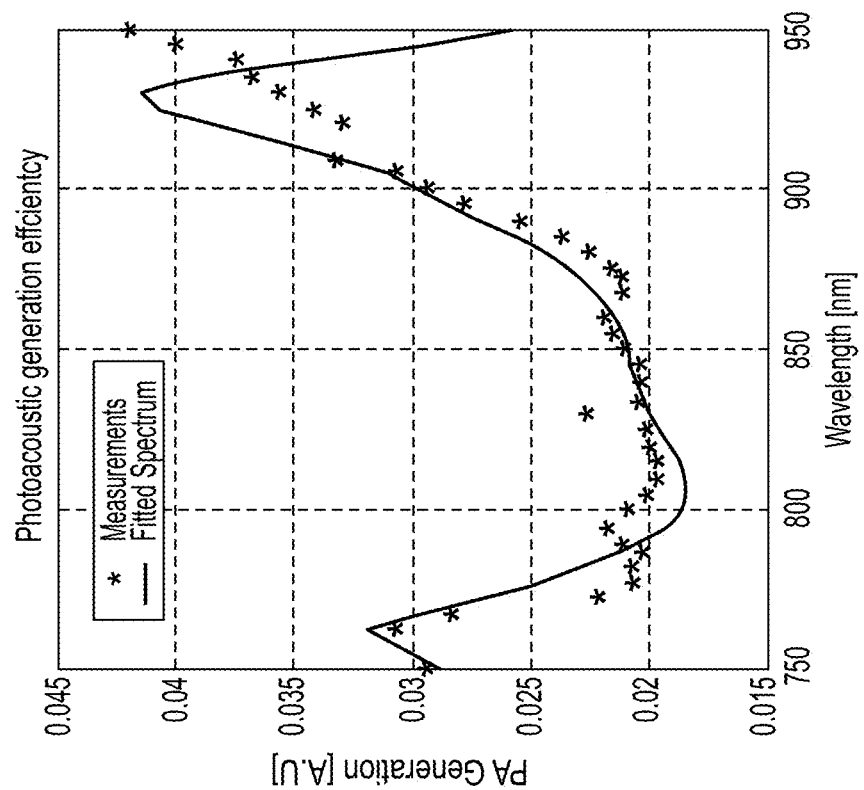
FIG. 8

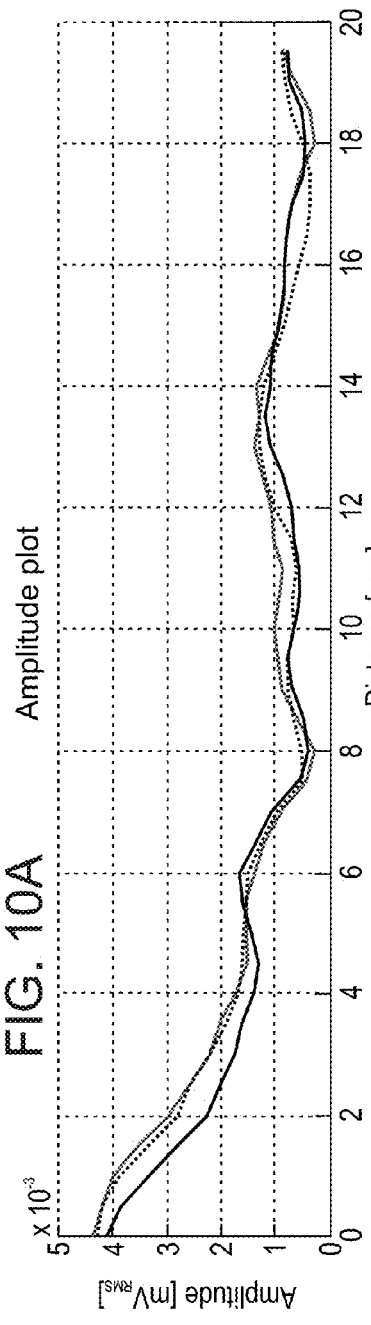
FIG. 10A
FIG. 10B
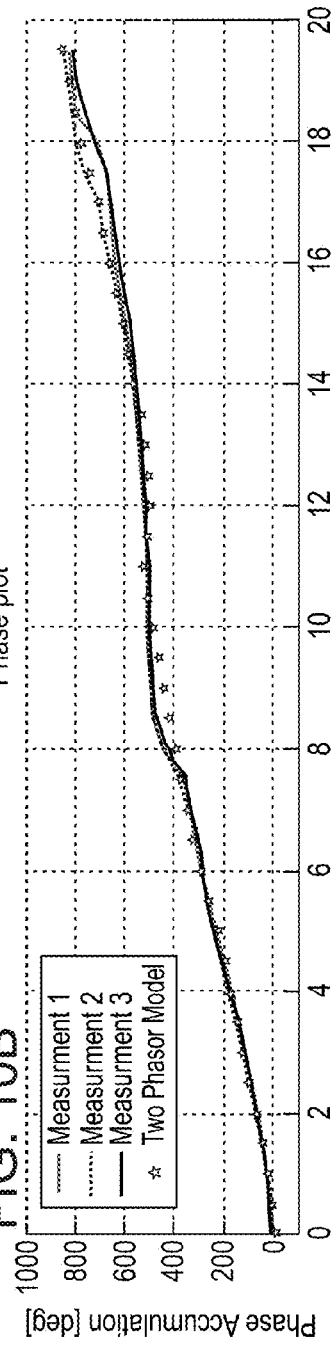
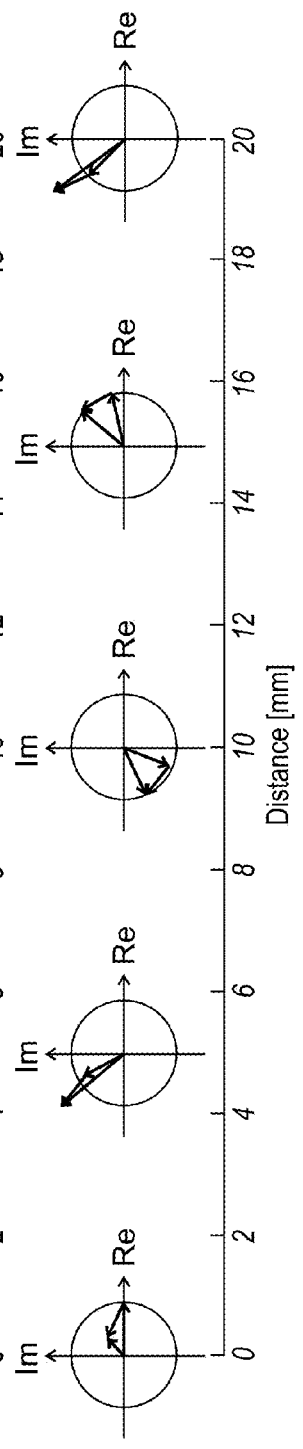
FIG. 10C

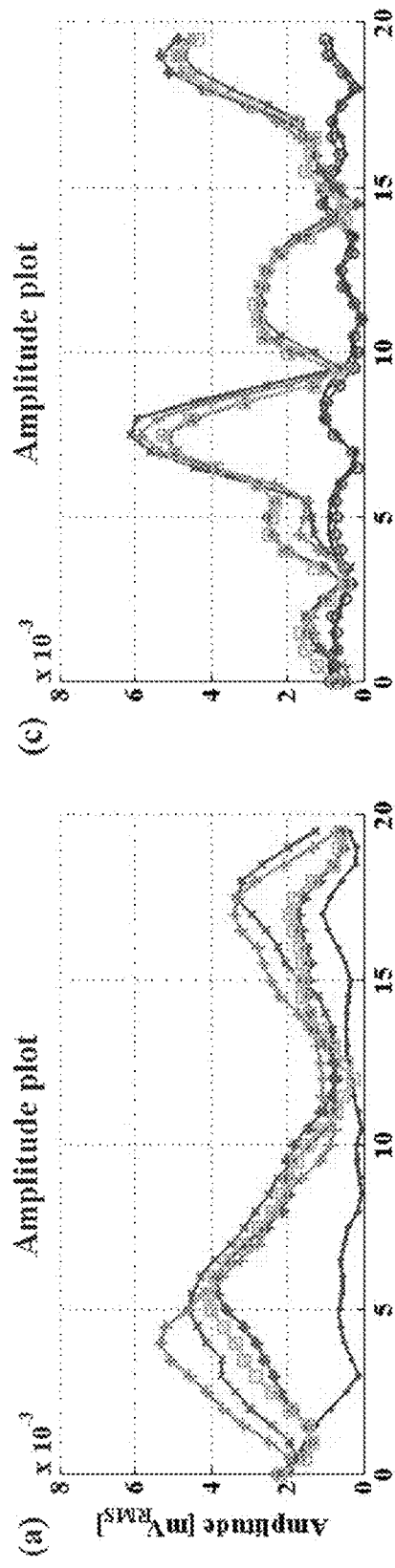
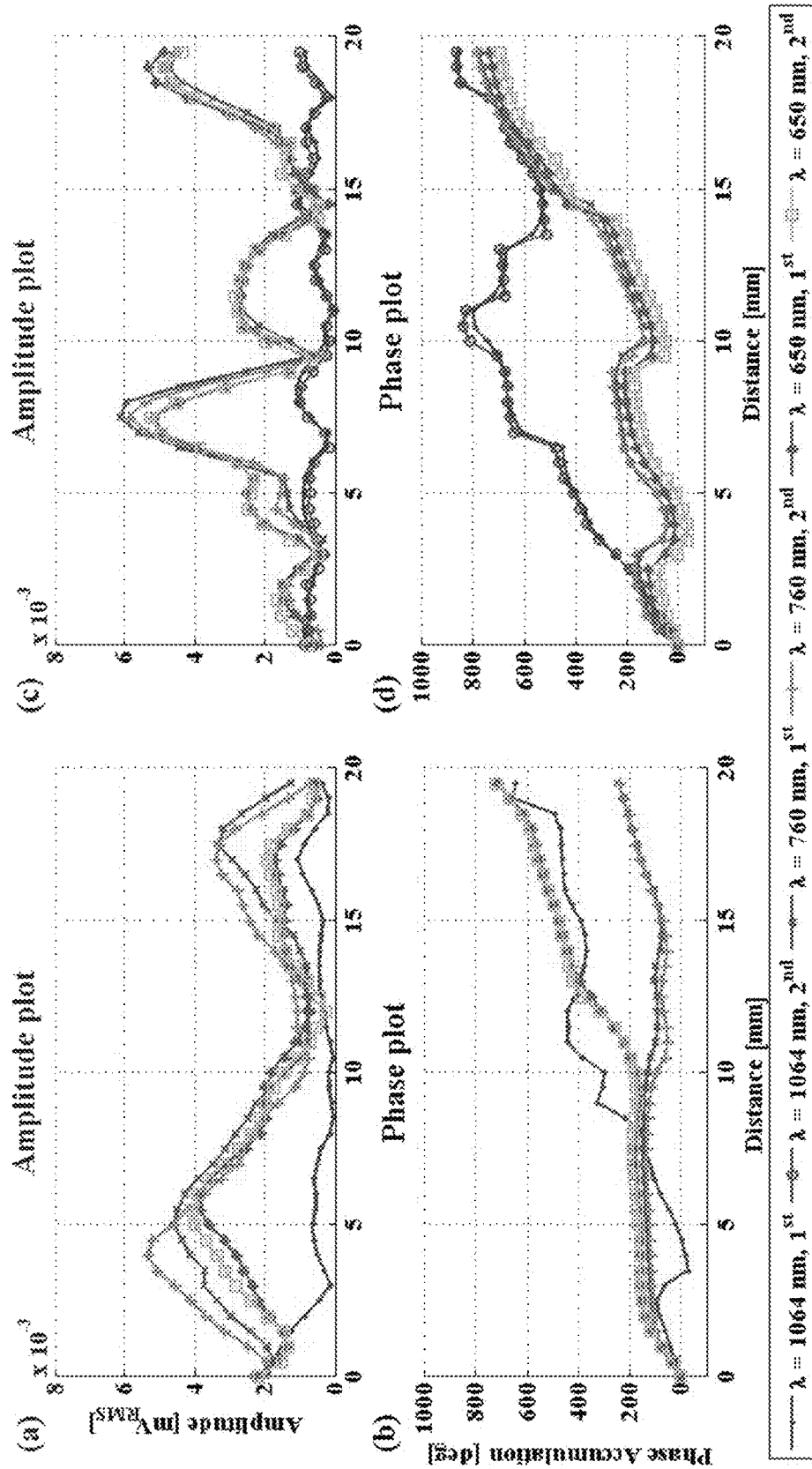
FIG. 11A
FIG. 11C
FIG. 11B
FIG. 11D

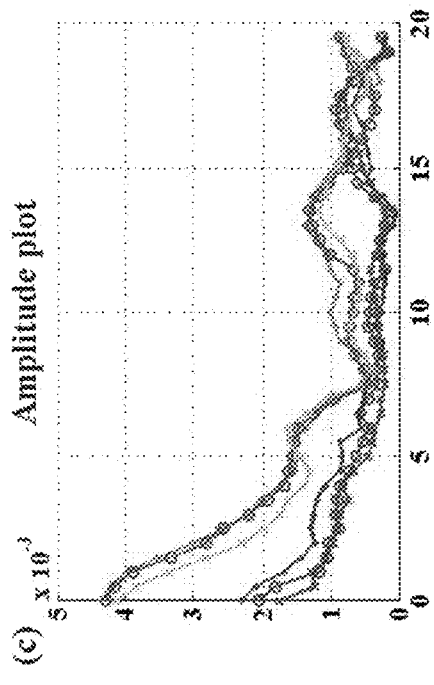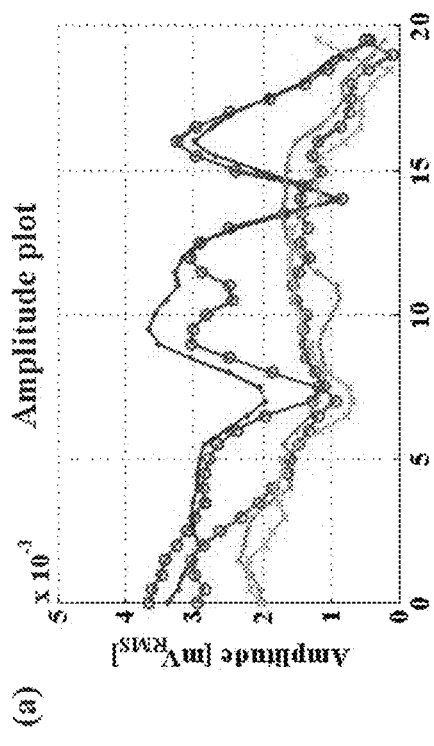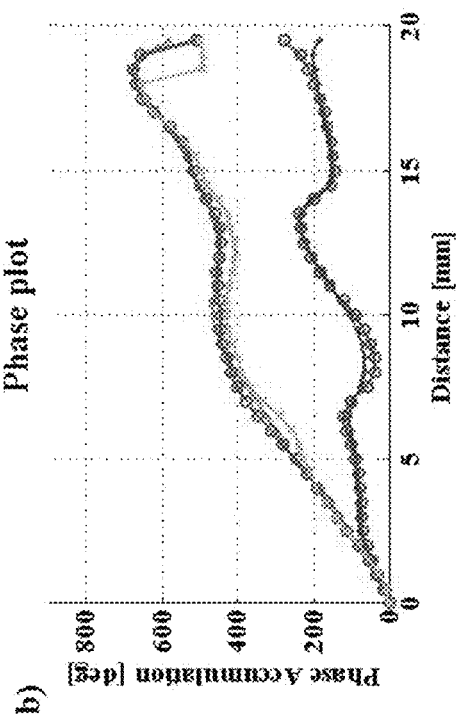
FIG. 12A  FIG. 12C
FIG. 12B  FIG. 12D

DETECTION, DIAGNOSIS AND MONITORING OF OSTEOPOROSIS BY A PHOTO-ACOUSTIC METHOD

RELATED APPLICATIONS

This application is a National Phase of PCT Patent Application No. PCT/IL2014/050108 having International filing date of Jan. 30, 2014, which claims the benefit of priority under 35 USC §119(e) of U.S. Provisional Patent Application No. 61/758,787 filed on Jan. 31, 2013. The contents of the above applications are all incorporated by reference as if fully set forth herein in their entirety.

FIELD AND BACKGROUND OF THE INVENTION

The present invention, in some embodiments thereof, relates to a method and apparatus for the detection, diagnosis and monitoring of osteoporosis and, more particularly, but not exclusively, to such a method and apparatus that does not require ionizing radiation.

Osteoporosis is a skeletal disorder characterized by compromised bone strength predisposing to an increased risk of fracture. It is widely acknowledged that bone strength and resistance to fracture depend, not only on the Bone Mineral Density (BMD), but also on the bone quality—its architecture, turnover rate, micro-fractures and degree of mineralization. The disease is extremely widespread: more than 1 in 3 women and 1 in 5 men will sustain at least one osteoporotic fracture in their lifetimes. By comparison, a woman's risk of breaking a hip due to osteoporosis is equal to her risk of breast, ovarian and uterine cancer combined, a man at age 50 or older is more likely to break a bone due to osteoporosis than he is to get prostate cancer. The consequences of fractures are fearsome—50% of all patients suffering from a hip fracture will never walk again and 20% of all patients suffering from a hip fracture will die within one year.

The disease is considered a major public health problem worldwide due to the number of fractures and the related overwhelming healthcare costs—tens of billions of dollars annually. By comparison, the healthcare costs of all osteoporosis-related fractures is currently equivalent to the healthcare costs of all cardiovascular disease and asthma combined. The vast majority of patients are not diagnosed until the osteoporosis is fully developed and fracture occurs that requires long term treatments. Identifying and treating patients at risk of fracture, but who have not yet sustained a fracture, can substantially reduce the five-year fracture incidence and related healthcare costs accordingly.

Currently, the Dual-energy X-ray Absorptiometry (DXA) method, which measures the BMD, is the gold standard measurement and the clinically accepted screening tool. However, DXA is inefficient for detecting bone loss at women younger than 60, it is costly many tens of USD per test) and involves ionizing radiation which causes patient non-compliance with the test. Since DXA measures only BMD and not bone quality, it can only predict the risk of 70% of all osteoporotic fractures and only for the elderly population where osteoporosis has fully developed. Bone loss may actually begin at the age of 30 but it is too small to be detected by DXA and it is extremely difficult to revert after osteoporosis has developed.

Thus, there is a need for non-invasive, non-ionizing and cost-effective screening tool to detect the disease as early as possible based on its pathological expressions and to monitoring disease progression during treatment.

An attempt to address some of the drawbacks of DXA is made using ultrasonic methods. Quantitative Ultrasound (QUS) represents an umbrella of techniques that attempt to characterize the biomechanical strength of bones by measuring the parameters of ultrasound transmitted through the bone in-vivo 11. Most QUS techniques measure some variants of Broadband Ultrasonic Attenuation (BUA) or the Speed of Sound (SOS) of the ultrasonic pulse propagating through the bone. These parameters correspond to the amplitude and phase of the ultrasonic transfer function of the bone.

Theoretical models have shown that these parameters are affected by both bone density and microstructure and thus, at least on theoretical grounds, provide a better estimate of the risk of fracture. However, clinical use QUS has yet to demonstrate superiority over DXA or to show statistically significant successes in assessing the bone functional status. The reason for this might be the inherent insensitivity of ultrasound to molecular and functional changes in the tissue.

In contrast, optical methods are uniquely qualified for probing tissue functional status due to their inherent noninvasiveness and the highly informative content encoded in the spectral signatures of tissue constituents.

Attenburrow et al.—cited as Ugryumova, N., Matcher, S. J. & Attenburrow, D. P. Measurement of bone mineral density via light scattering, *Physics in medicine and biology* 49, 469 (2004)—have shown in-vitro that bone demineralization, such as present in osteoporosis, causes great changes in the absorption and scattering properties of the bone. Pifferi, A. et al. Optical biopsy of bone tissue: a step toward the diagnosis of bone pathologies. *Journal of Biomedical Optics* 9, 474 (2004) have shown in-vivo that the near Infrared (NIR) optical absorption and transmission through the calcaneus bone are dependent on the age of the subject and are related to the state of the bone. However, pure optical methods which rely upon scattered photons which escape the tissue through transmission or back reflection are limited in their imaging depth or resolution due to their reliance on very weak signals. This is especially true in bone tissue where the overwhelming scattering ($\mu s\_150$ cm−1 at NIR wavelengths 18) greatly restricts the number of photons reaching the detector.

Photoacoustic (PA) imaging is renowned for its ability to produce high resolution in-vivo images at depths where none of the other optical bio-imaging techniques can. PA signals carries information about the molecular content and functional state at the absorption sites due to the direct dependence of PA signal generation on the absorption properties of the medium.

When a short laser pulse irradiates an absorbing medium there is local absorption, which leads to local heating and local expansion. This local expansion leads to ultrasonic pressure waves that travel through the medium at the speed of sound, and can be recorded using high frequency pressure sensors. The slow speed of sound in tissue (~1500 m/s) in comparison to the speed of light allows for the time resolved detection of these pressure waves and the determination of depth from where these pressure waves originated. By using an array of sensors the temporal delay of the incoming pressure wave fronts can be combined into an ultrasound image.

Although the technology is still in its infancy, photoacoustic imaging is being employed in the development of various devices. Such devices include breast cancer detection equipment, as well as equipment used for measuring oxygenation levels. In both cases, the change in the optical properties of blood in respect to oxygen saturation and the strong optical contrast between hemoglobin and surrounding tissue is utilized. Recently, Zhao et al. have demonstrated single wavelength photoacoustic excitation and detection on bone samples coated with Gelatin. They used low frequency ultrasound of 50 kHz to investigate the slow Fundamental Flexural Guided Wave.

SUMMARY OF THE INVENTION

As discussed above, osteoporosis is a major health problem worldwide, with healthcare costs of billions of dollars annually. The risk of fracture depends on the bone mineral density (measured in clinical practice) as well as on the bone microstructure and functional status. Pure ultrasonic methods can measure bone strength and spectroscopic optical methods can provide valuable functional information.

The present embodiments combine optical and ultrasonic methods and furthermore provide a hybrid multispectral photoacoustic technique.

According to an aspect of some embodiments of the present invention there is provided apparatus for examining bone in vivo, comprising:

a laser source configured to produce a laser beam; a modulator, configured to modulate the laser beam at acoustic frequencies being frequencies that are able to give rise to acoustic waves;

a waveform generator configured to drive the modulator with a modulation signal at a range of the acoustic frequencies, thereby to produce a multiple frequency acousto-optic beam able to cause excitation at a plurality of frequencies;

a spectrum analyzer, located to analyze received signals from the bone, the received signals including signals resulting from acoustic waves traveling within the bone caused by the modulated multiple frequency photoacoustic beam, the analyzing being to determine a mineral density and a bone quality for the bone.

In an embodiment, the spectrum analyzer is configured to analyze the received signal at optical wavelengths and acoustic frequencies.

In an embodiment, the scanning is carried out to map a bone transfer function, and further to analyze amplitude and phase along an acoustic frequency axis to determine a speed of sound dispersion and a broadband ultrasonic attenuation, therefrom to determine the mineral density and the bone quality.

An embodiment may use the bone transfer function, the speed of sound dispersion and the broadband ultrasonic attenuation to determine biochemical composition of the bone.

An embodiment may comprise a beam director to direct the laser beam towards the bone at an excitation point separated from a measurement point, such that acoustic waves enter the bone substantially at the excitation point and travel down the bone to the measurement point.

An embodiment may comprise an ultrasonic transducer located on the limb at the measurement point to measure ultrasonic wave propagation at the measurement point.

An embodiment may serve to integrate an ultrasonic system onto a photoacoustic system.

In an embodiment, the integration is achieved by selecting the frequency range for the photoacoustic signals to be at or above half a megahertz.

In an embodiment, the analyzing is configured to obtain a measurement of QUS parameters of the bone and a measurement of the NIR absorption spectrum of the bone.

According to a second aspect of the present invention there is provided a method for examining bone in vivo, comprising:

obtaining a laser beam;

modulating the laser beam at photoacoustic frequencies, including acoustic frequencies being able to give rise to acoustic waves, the modulating comprising inserting a plurality of the photoacoustic frequencies;

directing the modulated beam at a bone to cause acoustic waves caused by the beam to travel through the bone at a plurality of frequencies;

analyzing received signals from the bone, the received signals including signals resulting from the acoustic waves traveling within the bone, the analyzing being to determine a mineral density and a bone quality for the bone.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

The signal processing, measurement and analysis aspects of the present embodiments, can involve performing or completing selected tasks manually, automatically, or a combination thereof. Moreover, according to actual instrumentation and equipment of embodiments of the method and/or system of the invention, several selected tasks could be implemented by hardware, by software or by firmware or by a combination thereof using an operating system.

For example, hardware for performing selected tasks according to embodiments of the invention could be implemented as a chip or a circuit. As software, selected tasks according to embodiments of the invention could be implemented as a plurality of software instructions being executed by a computer using any suitable operating system. In an exemplary embodiment of the invention, one or more tasks according to exemplary embodiments of method and/or system as described herein are performed by a data processor, such as a computing platform for executing a plurality of instructions. Optionally, the data processor includes a volatile memory for storing instructions and/or data and/or a non-volatile storage, for example, a magnetic hard-disk and/or removable media, for storing instructions and/or data. Optionally, a network connection is provided as well. A display and/or a user input device such as a keyboard or mouse are optionally provided as well.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings:

FIG. 1 is a simplified block diagram showing apparatus according to a first generalized embodiment of the present invention;

FIG. 2 is a simplified flow chart showing operation of an embodiment of the present invention;

FIG. 3 is a simplified block diagram showing the embodiment of FIG. 1 in greater detail;

FIG. 4 is a simplified diagram block diagram showing an experimental apparatus for testing the analysis of the present embodiments;

FIG. 5 is a simplified diagram block diagram showing a second experimental apparatus for testing the analysis of the present embodiments;

FIG. 6 is a series of three graphs that describe measured phases from fowl bone before and after acid treatment in naïve and dematerialized bone for frequencies of 440 kHz, 480 kHz and 520 kHz respectively using embodiments of the present invention, and comparing the model with actual measurements;

FIG. 7 is a series of three graphs of normalized signal amplitude v distance showing ultrasonic attenuation in naïve and dematerialized bone for 440, 480 and 520 kHz are taken, comparing the model with actual measurements. According to the present embodiments;

FIG. 8 is a series of two graphs showing results of the multispectral photoacoustic excitation of a rat tibia according to the present embodiments on the left, and on the right, for comparison, showing absorption spectra of several other tissue chromophores such as oxy and deoxy-hemoglobin, water and fat;

FIG. 9 illustrates a variation of the experimental apparatus of FIG. 4 using multiple single wavelength laser sources;

Figure 1:
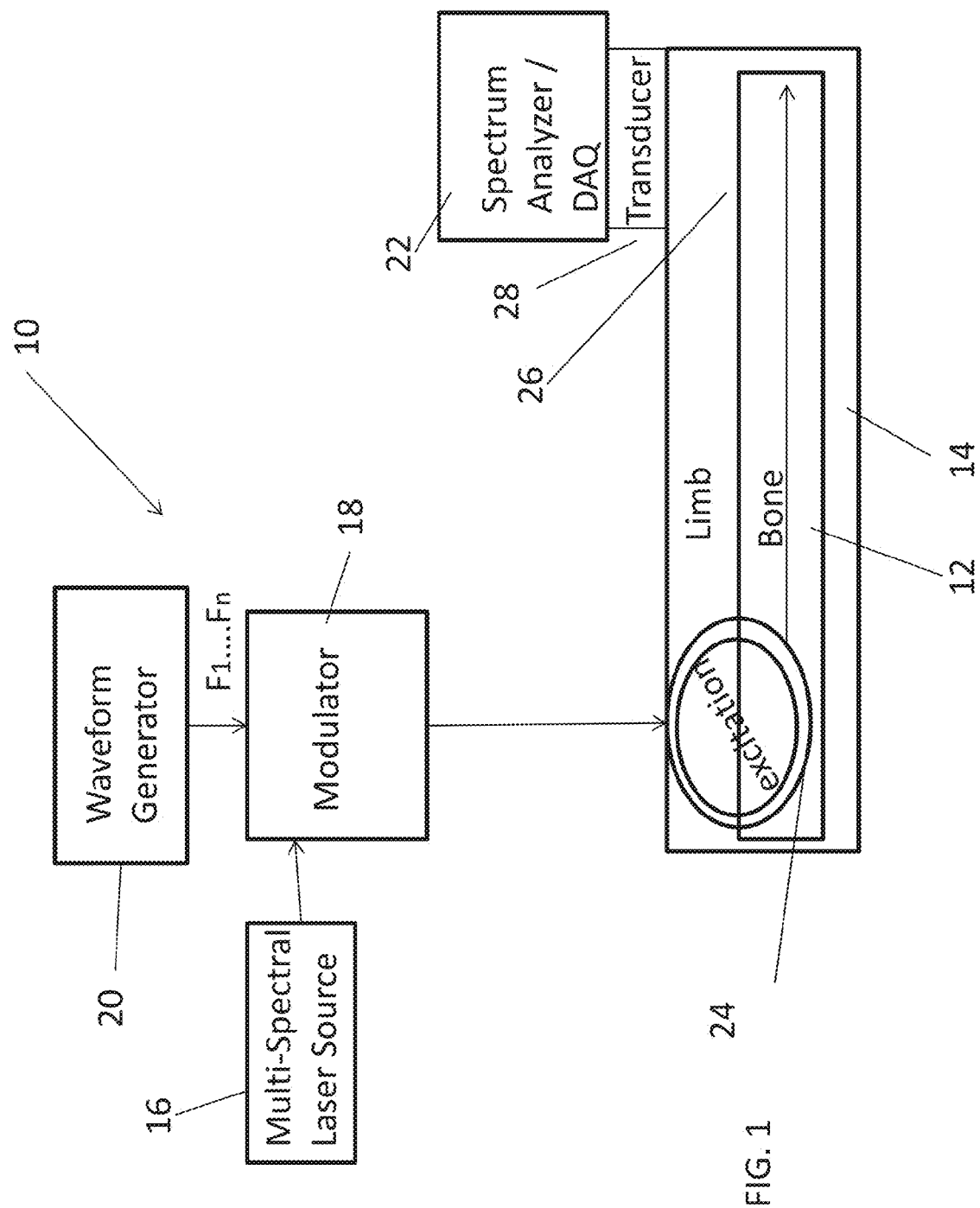

FIGS. 10A-C are simplified graphs illustrating separate amplitude and phase plots against models for an embodiment of the present invention;

FIGS. 11A-D are simplified graphs showing amplitude and phase plots for different wavelength according to embodiments of the present invention from which a BMD may be calculated; and FIGS. 12A-D are simplified graphs showing amplitude and phase plots for different wavelengths before and after an induced osteoporotic process.

DESCRIPTION OF SPECIFIC EMBODIMENTS OF THE INVENTION

The present invention, in some embodiments thereof, relates to a method and apparatus for the detection, diagnosis and monitoring of osteoporosis and, more particularly, but not exclusively, to such a method and apparatus that does not require ionizing radiation.

As explained above, photoacoustic (PA) imaging is renowned for its ability to produce high resolution in-vivo images at depths where none of the other optical bio-imaging techniques can. PA signals carry information about the molecular content and functional state at the absorption sites due to the direct dependence of PA signal generation on the absorption properties of the medium. In the present embodiments, such information may be gathered by using several excitation wavelengths (Multispectral Photo-Acoustics) and implementation of spectroscopic tools for substance analysis. Thus, photoacoustic measurements may offer an advantage over pure ultrasound (US) methods as they allow measurement of all QUS parameters as well as the measurement of the NIR absorption spectrum of the tested bone.

Before explaining at least one embodiment of the invention in detail, it is to be understood that the invention is not necessarily limited in its application to the details of construction and the arrangement of the components and/or methods set forth in the following description and/or illustrated in the drawings and/or the Examples. The invention is capable of other embodiments or of being practiced or carried out in various ways.

Referring now to the drawings, FIG. 1 illustrates apparatus 10 for examining bone 12 in vivo within limb 14.

A multi spectral laser source 16 produces a laser beam with a defined wavelength. An internal or external modulator 18 (here shown as external) modulates the laser beam at ultrasonic frequencies $f_1 \ldots f_n$. The ultrasound frequencies in particular are frequencies that are able to give rise to acoustic waves that may travel through the bone.

Waveform generator 20 drives the modulator with a modulation signal to insert the range of frequencies described above. The output of the modulator may thus be a multiple frequency acousto-optic beam, and the beam as a whole is able to cause acoustic excitation at multiple frequencies to provide acoustic waves that may travel through bone.

A DAQ or a spectrum analyzer 22 analyzes received signals from the bone. The received signals are acoustic signals resulting from acoustic waves within the bone caused by the modulated multiple frequency photoacousticoptical beam. The analyzing may determine a mineral density and a bone quality for the bone, as will be discussed in greater detail below.

The spectrum analyzer 22 may measure different acoustic frequencies and the optical source might be set to scan different optical wavelengths to map a bone transfer function. The analyzer 22 may analyze amplitude and phase along an acoustic frequency axis to determine a speed of sound dispersion and a broadband ultrasonic attenuation, and from this analysis may be able to determine the mineral density and the bone quality.

The apparatus 10 may further use the bone transfer function, the speed of sound dispersion of the bone and the broadband ultrasonic attenuation to determine the biochemical composition of the bone 12.

The modulator may further provide a beam director to direct the modulated laser beam towards the bone at a selected point 24, referred to herein as the excitation point. The excitation point is separated from a measurement point 26, located at a certain distance along the bone. A primary wave may travel along the bone approximately from the excitation point to be sampled at the measurement point.

An ultrasonic transducer 28 may be located on the limb opposite measurement point 26 to sample the ultrasonic wave propagation at the measurement point for analysis by the spectrum analyzer.

As will be discussed below, the present embodiments may provide an integration of an ultrasonic system onto a photoacoustic system. Such an integration may be achieved by selecting the frequency range for the photoacoustic signals to be at and above half a megahertz.

The analysis may obtain a measurement of QUS parameters of the bone and a measurement of the NIR absorption spectrum of the bone.

Figure 2:
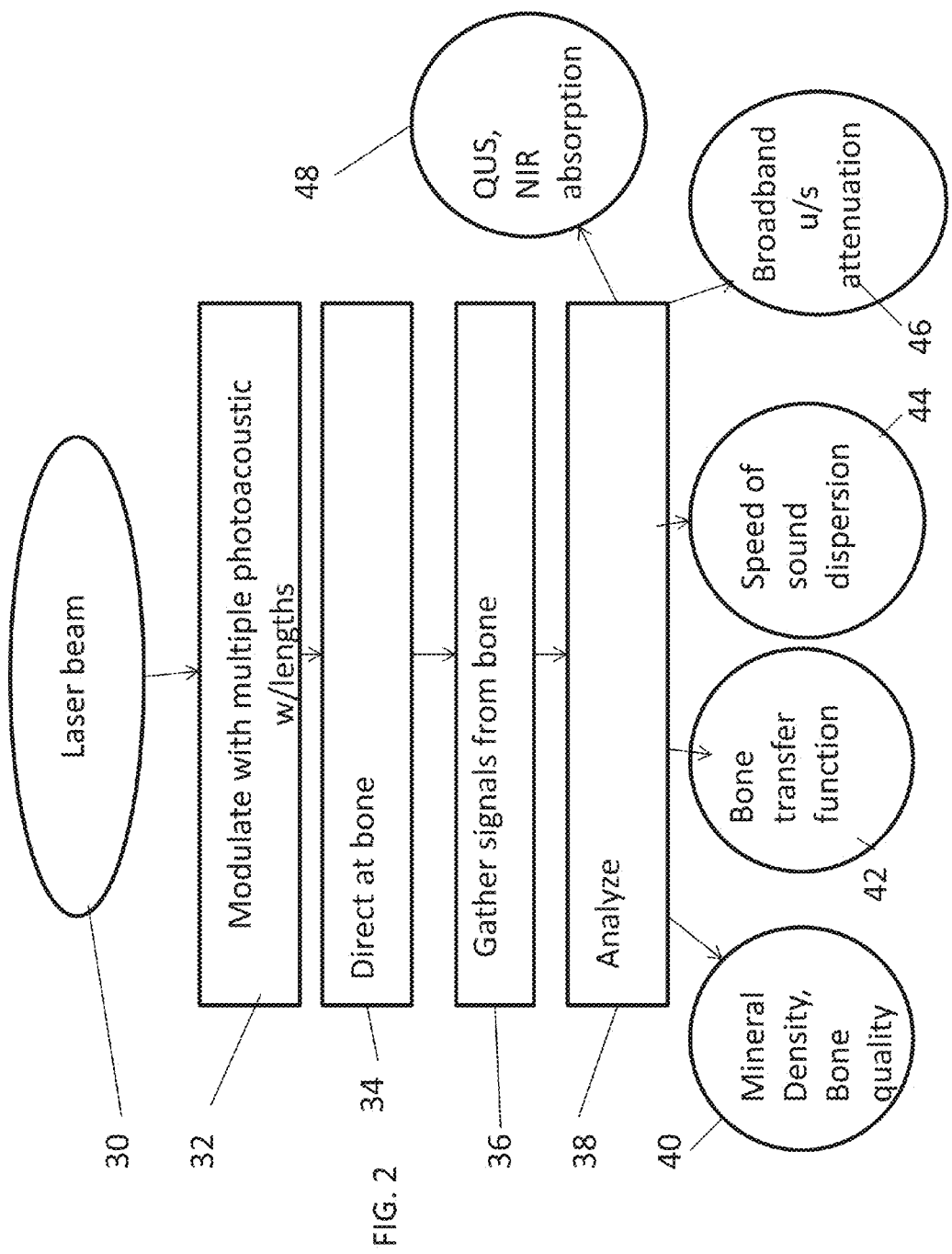

Reference is now made to FIG. 2, which is a simplified flow chart illustrating how a method for examining bone in vivo may be carried out.

Initially a laser beam is provided 30. The beam is modulated 32 to insert therein photoacoustic frequencies. As discussed, the acoustic frequencies, typically ultrasonic frequencies, may give rise to acoustic waves that may travel along the bone, and multiple frequencies are used.

The modulated beam is directed 34 towards a point on the bone, or on the flesh of the limb covering the bone, so as to allow light and ultrasound resulting from optical excitation to travel through the wave.

The limb is monitored and signals received from the bone are gathered or transduced 36 and analyzed 38. The received signals include signals resulting from acoustic waves caused by excitation of the optical beam, the acoustic waves having traveled through a length of bone. Analyzing is carried out as discussed below to determine 40 a mineral density and a bone quality.

The analyzing may typically involve scanning optical wavelengths and acoustic wavelengths to map 42 a bone transfer function. Analysis of amplitude and phase along an acoustic frequency axis may provide 44 a speed of sound dispersion and a broadband ultrasonic attenuation 46, and these may be used to obtain the mineral density and the bone quality 40.

More specifically, the bone transfer function, the speed of sound dispersion and the broadband ultrasonic attenuation may be analyzed to determine the biochemical composition of the bone.

As explained, the modulated beam may be directed at a specific point on the bone, or the flesh covering the bone. The point is separated from a measurement point, so that waves generated inside the bone at or around the excitation point travel down the bone to the measurement point over a distance that allows the waves to be affected by the bone qualities.

The analyzing may obtain 48 a measurement of QUS parameters of the bone and a measurement of the NIR absorption spectrum of the bone.

It is particularly pointed out that the method shown in FIG. 2 is not a method of diagnosis, but is merely a method of obtaining data about individual bones that may be of assistance, together with other data, to assist a doctor in diagnosing osteoporosis.

Figure 3:
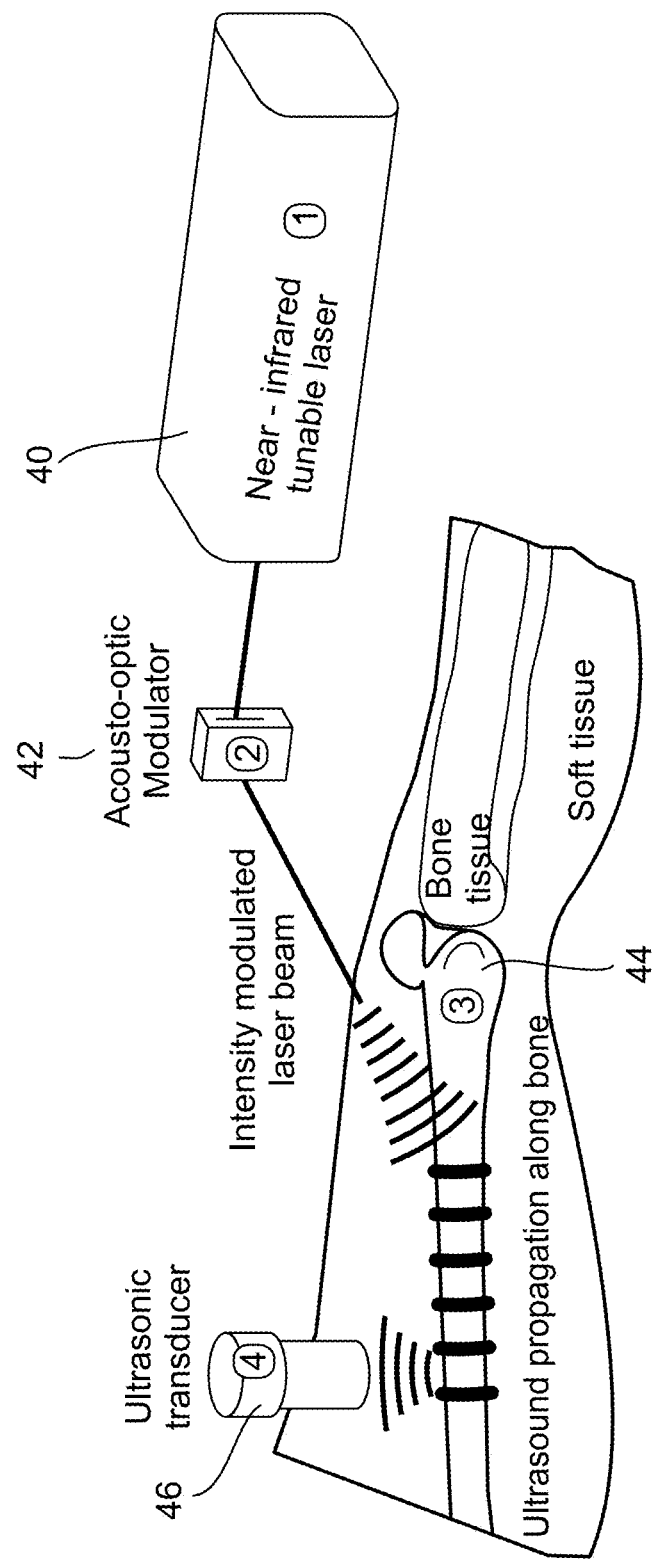
Figure 4:
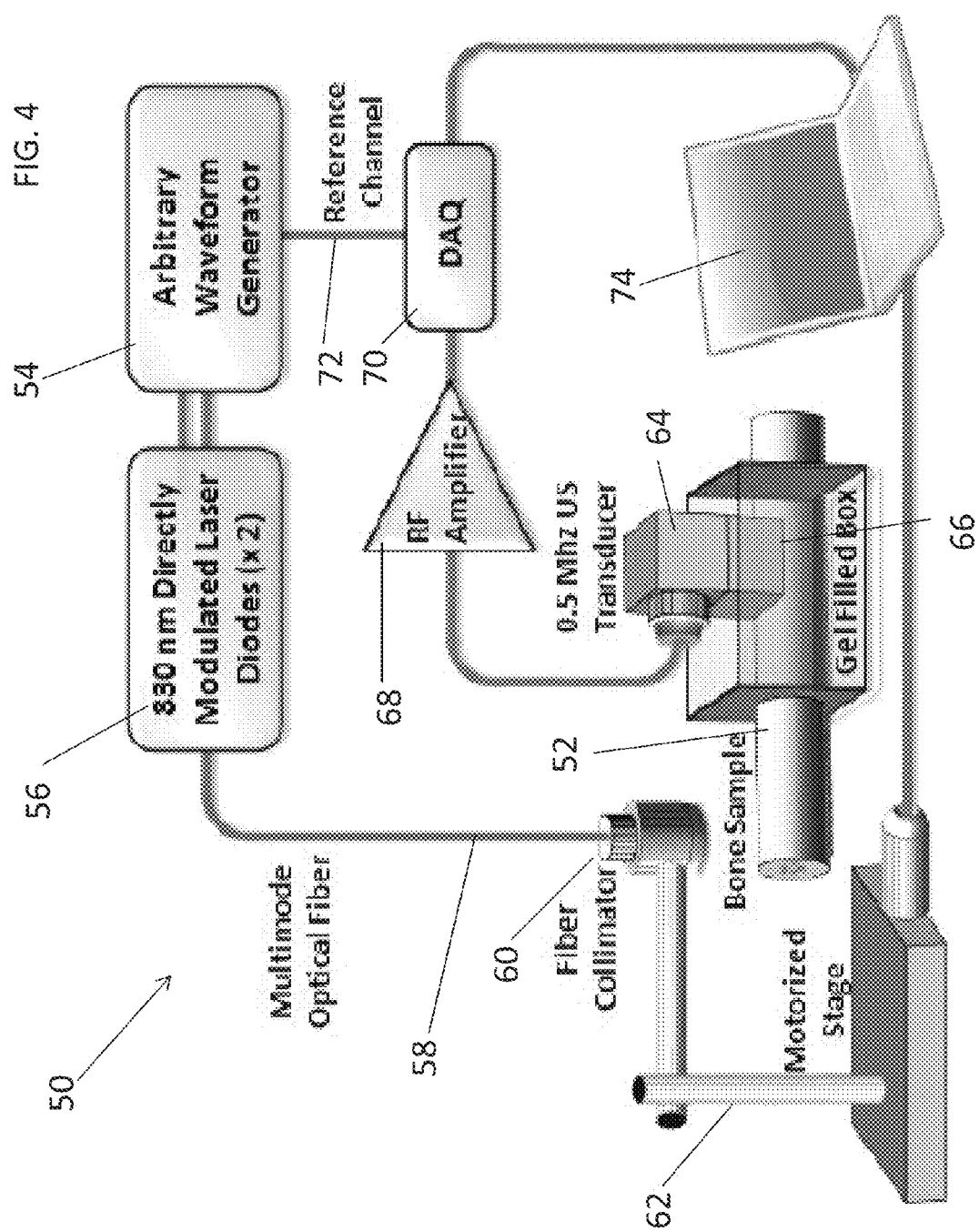
Figure 5:
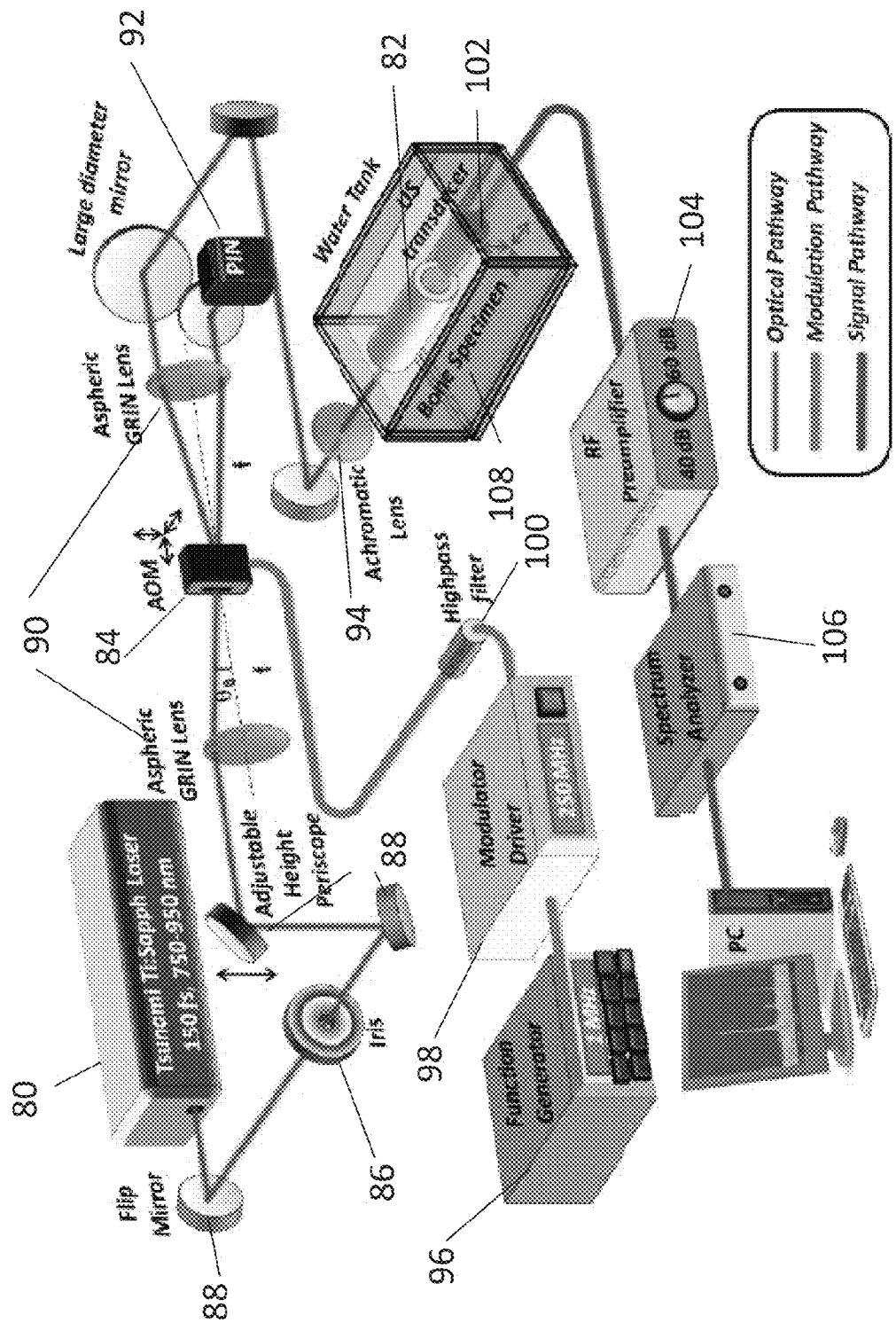
Figure 9:
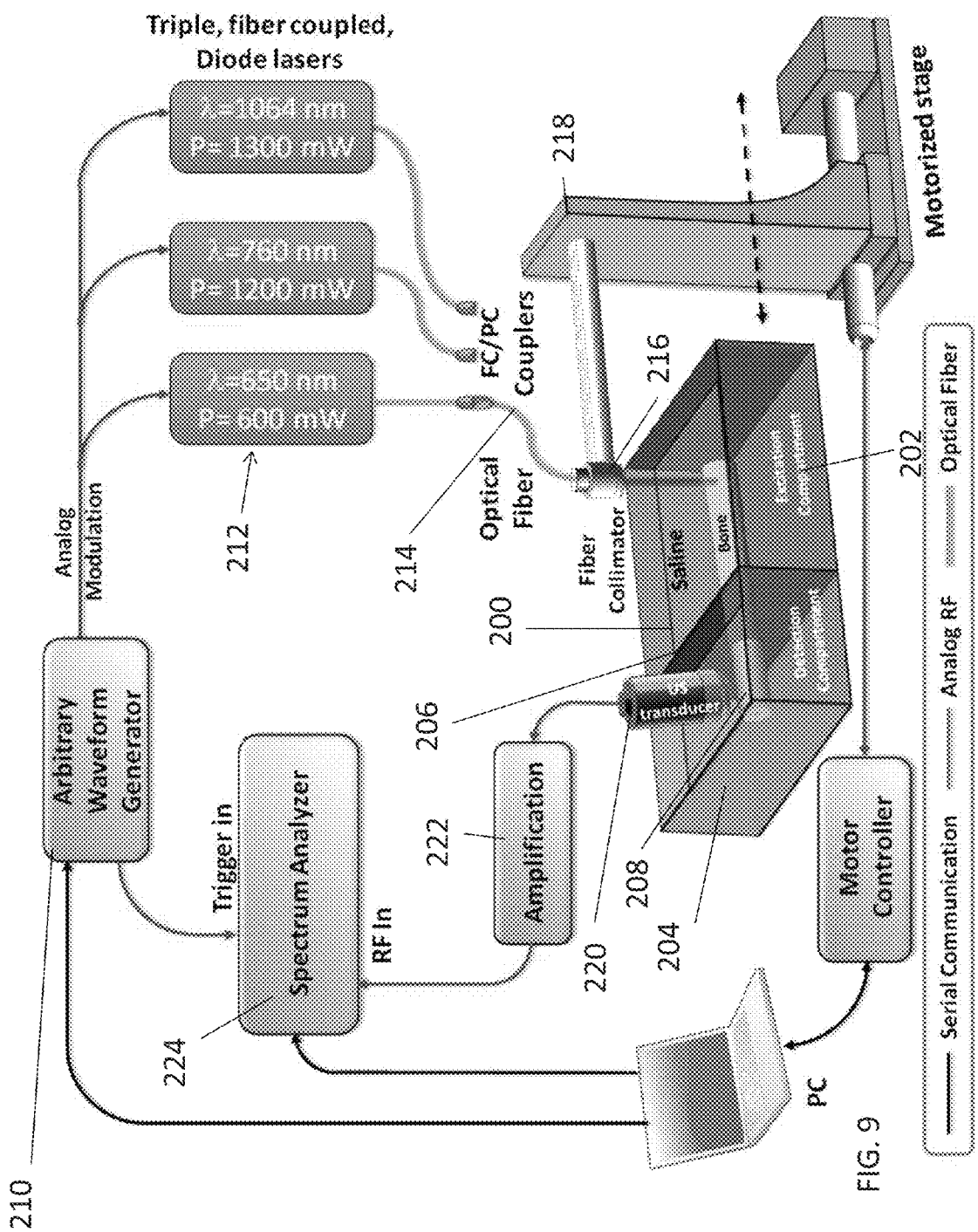

It is noted that, in general, the excitation wavelength is determined solely by the laser source, and the modulator is completely is irrelevant for the choice of wavelength. Thus, the optical source may be a multi-spectral optical source— see FIG. 4 but compare with FIG. 9 hereinbelow. Such a source can be realized by a tunable laser, as shown in FIGS. 3 and 5, or by multiple single wavelength sources as shown in FIG. 9. The latter may be advantageous as a multitude of laser diodes is usually less expensive and more flexible then a single tunable laser. A tunable laser is thus not necessary for the present embodiments.

The sole function of the modulator is to accept an optical beam with a particular wavelength, determined by the source as explained above, and modulate the intensity with suitable ultrasound frequencies (0.5-2.5 MHz). The use of a Modulator is only one embodiment and is not essential for the present embodiments. An Electro-optic modulator, a chopper or any other form of intensity modulation may be used instead. In the embodiments described in FIGS. 4 and 9 the modulation is internal, that is to say the optical source itself generates the laser beam with modulated intensity, thus simplifying the apparatus.

Signals may be analyzed in the frequency domain. However, they can be acquired either in the time domain by a data acquisition (DAQ) or directly in the frequency domain by a spectrum analyzer. A spectrum analyzer is thus not essential for the present embodiments.

The ultrasound transducer is the only sensor that is needed and it is only sensitive to ultrasonic waves generated in the tissue, which may be both soft and hard tissue, due the intensity modulated optical beam. The spectrum analyzer or any other device does not measure anything optical. The strength of acoustic waves is related to the product of the laser peak intensity by the tissue optical absorption coefficient. Thus by measuring the intensity of the acoustic waves in different optical wavelengths one can deduce the optical spectrum of the bone.

It is noted that the terms "Optoacoustic" and "Photoacoustic" are synonymous. The present text uses the term "Photoacoustic", only for consistency.

Reference is now made to FIG. 3, which is a simplified diagram illustrating an arrangement for the apparatus of FIG. 1. As discussed, the present embodiments may extend the current ultrasonic methods into a hybrid Multispectral Photoacoustic technique for non-invasive, in-vivo simultaneous measurements of both bone gross chemical content and mechanical resistance to fracture. The apparatus, as shown, utilizes a tuneable NIR laser source 40 followed by a Modulator 42 to optically excite ultrasound waves which propagate along the bone axis 44. A spectrum analyzer with tracking generator is used for measuring both the amplitude and the phase at the distal end of the bone. Scanning along both the optical wavelength as well as the acoustic frequency enables full mapping of the bone transfer function. Analyzing the bone transfer function along the wavelength axis allows deducing of the gross biochemical composition related to the bone functional and pathological state. Analyzing the amplitude and phase along the acoustic frequency axis yields the speed of sound dispersion and the broadband ultrasonic attenuation—both have shown clinical relevance.

As shown, the modulated laser beam is incident upon the skin surface. A portion of the beam is absorbed by the bone tissue, generating an ultrasonic wave within the bone which propagates along the bone axis and is picked up by a transducer.

It is widely accepted that long bones with thick cortex act as a waveguide for transmitting ultrasonic waves with relatively low attenuation. The theory of flexural and longitudinal Rayleigh-Lamb waves in an irregular cylindrical structure with anisotropic elastic properties, and thus being representative of bone, is extremely complicated and predicts the existence of many dispersive interacting modes. However, most experimental reports phenomenologically concern waves of only two kinds: weak and fast circumferential waves (also known as First Arriving Signal—FAS) and the stronger and slower guided wave (also known as Energetic Late Arrival—ETA).

As mentioned in the background, recently, Zhao et al. have demonstrated single wavelength photoacoustic excitation and detection on bone samples coated with Gelatin. They used low frequency ultrasound of 50 kHz to investigate the slow Fundamental Flexural Guided Wave.

The present embodiments go beyond Zhao in using multiple frequencies. Furthermore, in general, the present embodiments make measurements in ultrasonic frequencies around 0.5 MHz which are more conventional in QUS and allow the integration of a photoacoustic system onto existing ultrasound machines. The present embodiments may also characterize the photoacoustically generated ultrasound waves in the frequency domain and in multiple wavelengths, which allows a more complete assessment of bone functionality.

It was empirically found that a model based on two guided modes is sufficient to describe the measured amplitude and phase of the generated CW waves.

METHODS AND EXPERIMENTAL SETUP

A particular embodiment provides a system based on a tunable Ti:Sapph laser at 750-950 nm, followed by a modulator to generate photoacoustic signals with frequencies of 0.5-2.5 MHz.

A second embodiment was based on two directly modulated 830 nm laser diodes. The systems were used to photoacoustically excite the proximal end of a rat tibia. A spectrum analyzer with tracking generator was used for measuring both the amplitude and the phase at the distal end. Scanning along both the optical wavelength and the acoustic frequency may enable full mapping of the bone transfer function. Analyzing the bone transfer function along the wavelength axis may allow deducing of the gross biochemical composition related to the bone functional and pathological state. Analyzing the amplitude and phase along the acoustic frequency axis yields the speed of sound dispersion and the broadband ultrasonic attenuation—both have shown clinical relevance.

Frequency domain measurements of the phase and amplitude of photoacoustically generated ultrasound waves were performed. Single frequency phase measurements allow for greater accuracy in the measurement of the speed of sound (SOS) than the conventional time-domain methods which measures the Time Of Flight (TOF). This is due to the extreme dispersion present in the bone which renders the TOF measurement to be highly dependent on the SNR, the post measurement signal processing and the criterion for determining the exact time of arrival. When performing measurements in the frequency domain, electromagnetic interference is omni-present due to the electronics used to drive the optical excitation at the desired frequency. Thus, the signal received in the ultrasonic detector can be modelled as a sum of a phasor describing the EM interference and additional phasors which represents the guided modes that were excited by the modulated light. In the case of two significant guided modes the output signal can be described as:

$$P(x,f) = \underbrace{A_{EM} e^{i\varphi_{EM}}}_{\text{EM Phasor}} + \underbrace{A_{slow} e^{-\alpha_{slow} fx} e^{i[2\pi fx/c_{slow}(f) + \varphi_{slow}]}}_{\text{Slow Wave Phasor}} + \underbrace{A_{fast} e^{-\alpha_{fast} fx} e^{i[2\pi fx/c_{fast}(f) + \varphi_{fast}]}}_{\text{Fast Wave Phasor}}$$

where x is the distance from the transducer, f is the ultrasonic frequency, $A_{EM}$, $A_{slow}$ $A_{fast}$ are the amplitudes of the electromagnetic, slow and fast waves respectively, $\varphi_{EM}$, $\varphi_{slow}$, $\varphi f_{ast}$ are the constant phases of each phasor, $\alpha_{slow}$, $\alpha_{fast}$, are the attenuation coefficients (also known as the Broadband Ultrasonic Attenuation—BUA usually expressed in $dB \cdot MHz^{-1} \cdot cm^{-1}$) of the slow and fast waves and $c_{slow}(f)$, $c_{fast}(f)$ are the phase velocities of the slow and fast waves.

The electromagnetic interference phasor was found to be nearly constant throughout the experiment. Thus, it was possible to measure and subtract the interference phasor from the signal. In addition, to further reduce the complexity of the model it was assumed that $e^{-\alpha_{slow} fx} \approx e^{-\alpha_{fast} fx} \approx e^{-\alpha_{BUA} fx}$ over the small interval of the measurement: $x \in [x_i, x_f]$. This allowed decoupling between the phase and amplitude calculation of the slow and fast waves:

$$P - A_{EM} e^{i\phi_{EM}} = A(x,f) e^{i\phi(x,f)} = \\ A_0 e^{-\alpha_{BUA} fx} (e^{i[2\pi fx/c_{slow}(f) + \varphi_{slow}]} + \\ A_{fs} e^{-\alpha_{fast} fx} e^{i[2\pi fx/c_{fast}(f) + \varphi_{fast}]})$$

where A(x,f) and φ(x,f) are the measured amplitude and phase after reduction of the EM interference phasor and $A_{fs} = A_{fast}/A_{slow}$ is the relative amplitude between the two modes.

The analysis of the measured data was as follows: First we estimated the SOS and relative amplitude for each mode by fitting the measured phase φ(x,f) (after removal of the EM interference) using the following estimator:

$$[\hat{c}_{slow}, \hat{c}_{fast}, \hat{\varphi}_{slow}, \hat{\varphi}_{fast}, \hat{A}_{fs}] = \mathop{\text{argmin}}_{c_{slow}, c_{fast}, \varphi_{slow}, \varphi_{slow}, A_{fs}} \\ (\varphi(x,f) - \angle\{e^{i[2\pi fx/c_{slow}(f) + \varphi_{slow}]} + A_{fs} e^{i[2\pi fx/c_{fast}(f) + \varphi_{fast}]}\})^2$$

Then we found the common amplitude and Broadband Ultrasonic Attenuation by fitting the following measured amplitude using the following estimator:

$$[\hat{\alpha}_{BUA}, \hat{A}_0] = \mathop{\text{argmin}}_{\alpha_{BUA}, A_0} \\ (A(x,f) - A_0 e^{-\alpha_{BUA} fx} |e^{i[2\pi fx/c_{slow}(f) + \varphi_{slow}]} + A_{fs} e^{i[2\pi fx/c_{fast}(f) + \varphi_{fast}]}|)^2$$

Thus full characterization of the fast and slow modes was possible based on the measurements of the phase and amplitude as a function of distance along the bone, as well as measurement of the electromagnetic interference constant phase and amplitude.

To experimentally test the model in-vitro, a fiber-coupled laser diode based, single, wavelength photoacoustic system was developed. The system is described schematically in FIG. 4. FIG. 4 is a simplified block diagram illustrating an experimental setup 50 for measuring the speed of sound in bone. Fresh fowl radius bones 52 were used. Cartilage and surrounding soft tissue were removed with a scalpel. Bones were rinsed with water to remove blood and soft tissue leftovers. Bone length was roughly 5 cm from proximal to distal end with cortical thickness of ~1 mm. To generate the photoacoustic signal, an arbitrary Waveform Generator (Tektronix, AWG400) 54 was used for direct analog modulation of the intensity of adual, 830 nm laser diodes (Omicron, A350 series) 56. Modulation was sinusoidal with frequencies of 440, 480 and 520 kHz. The outputs of the laser diodes 56 were polarization combined and the resulting beam was coupled to a multimode fiber (50 μm core diameter, N.A 0.22) 58. The fiber output is collimated with affixed focus collimator (Thorlabs F220FC-780) 60 and the incident beam location on the distal end of the bone sample was selected using computer controlled 25 mm travel motorized translation stage (Thorlabs, PT1/M-Z8) 62. At each modulation frequency, the location of the beam was scanned along the bone over a 2 mm distance with 250 μm intervals. A 0.5 MHz, right angle ultrasonic immersion transducer (Olympus, IR-0008-P-RU) 64 was used to measure the ultrasonic waves in the proximal end 66 of the bone. To prevent any stray light to be reflected from the bone surface (due to small surface irregularities) and reach the transducer a specialized box 68 was used. Box 68 has a reflective outer coating and specialized holes are drilled to allow careful insertion of the bone and transducer through them as depicted in FIG. 4. The interior of the box is filled with ultrasound gel to allow better coupling of the transducer to the bone. It is noted that the distal part of the bone was floating in air due to the box geometry, thus ensuring that any photoacoustical signal received in the transducer results from the bone itself. The received signals were amplified by a series of RF amplifiers 68 (Olympus 5660B followed by Stanford Research Systems SR560).

Signals were sampled at 10M samples/sec rate over 5 seconds time intervals at DAQ 70. The resulting waveforms were then Fourier transformed and their phase and amplitude at the modulation frequency were calculated with respect to a reference channel 72 sampled directly from the AWG. The apparatus was controlled by computer 74. Upon completion of measurements at all frequencies, the bone was soaked in mild acetic acid for 2.5 hours to simulate the effect of osteoporosis. This process is known to dematerialize and thus weaken the strength of bones since the insoluble calcium reacts with the acetate to form calcium acetate, which is soluble and thus removed from the bone. It should be noted that complete removal of the calcium from the bone might take days.

Thus, a 2.5 hour acid treatment has a very gentle effect on bone strength. Upon completion of the acid treatment the bone was rinsed with water to remove any acid traces and all measurements were performed again for comparison.

Reference is now made to FIG. 5, which is a simplified block diagram illustrating the setup for a second experiment. In FIG. 5, the optical, RF modulation and US signal pathways are shown in different colors. Arrows mark components mounted on translation stages.

In the experiment of FIG. 5, the affects of different wavelengths on the efficiency of the photoacoustic generation were tested. To that end a PA setup was assembled based on a Ti:Sapph laser (Spectra Physics Lasers, Tsunami) 80. For this experiment 6 month old rat tibia bone 82 was used. Bone length was about 3 cm with cortical thickness of few hundred microns. The laser beam (shown in red) is directed to an AOM (AA Opto-Electronic, MT250-A0.12-800) 84. An iris (Thorlabs, SM2D25) 86, adjustable mirrors 88 and a 4f system using special aspheric GRIN lenses (Edmund Optics, NT47-457) 90 allow for the correct Bragg angle for efficient modulation. A portion of the beam was directed to a fast PIN detector (EOT, ET-2030) 92 for reference. The other portion was directed and focused by an achromatic lens 94 on the bone specimen in a water tank. To generate the 1 MHz modulation (modulation path shown in green) a function generator (Stanford Research Systems, DS335) 96 was used to control a voltage supplier (AA Opto-Electronic, MODA250-B51k-33) 98 or modulator driver followed by a RF highpass filter (Crystek, CHPFL-0100) 100 to reject noise at the modulation frequency. The ultrasonic signal (signal path shown in purple) is picked by an immersion transducer (Olympus, I3-0108-S-SU) 102 followed by a low-noise preamplifier (Olympus, 5660B) 104 and received by a Software Defined Radio (SDR) Spectrum Analyzer (Signal Hound, USB-SA44B) 106. To negate severe RF disturbances from the function generator 96, it was disconnected from the ground to prevent ground loops. In addition, to ensure that the photoacoustic signal was originating only from the bone sample rather than the sample holder and acoustic bath, a specialized mount was designed from transparent materials. The bone sample is harnessed on a pedestal, separated from the sample holder. The water tank 108 was cleared of water and the ultrasonic transducer 102 was placed ~3 cm away from the optical excitation along the bone axis. The photoacoustic response was measured over the 750-950 nm range with 5 nm intervals.

RESULTS AND DISCUSSION

Figure 6:
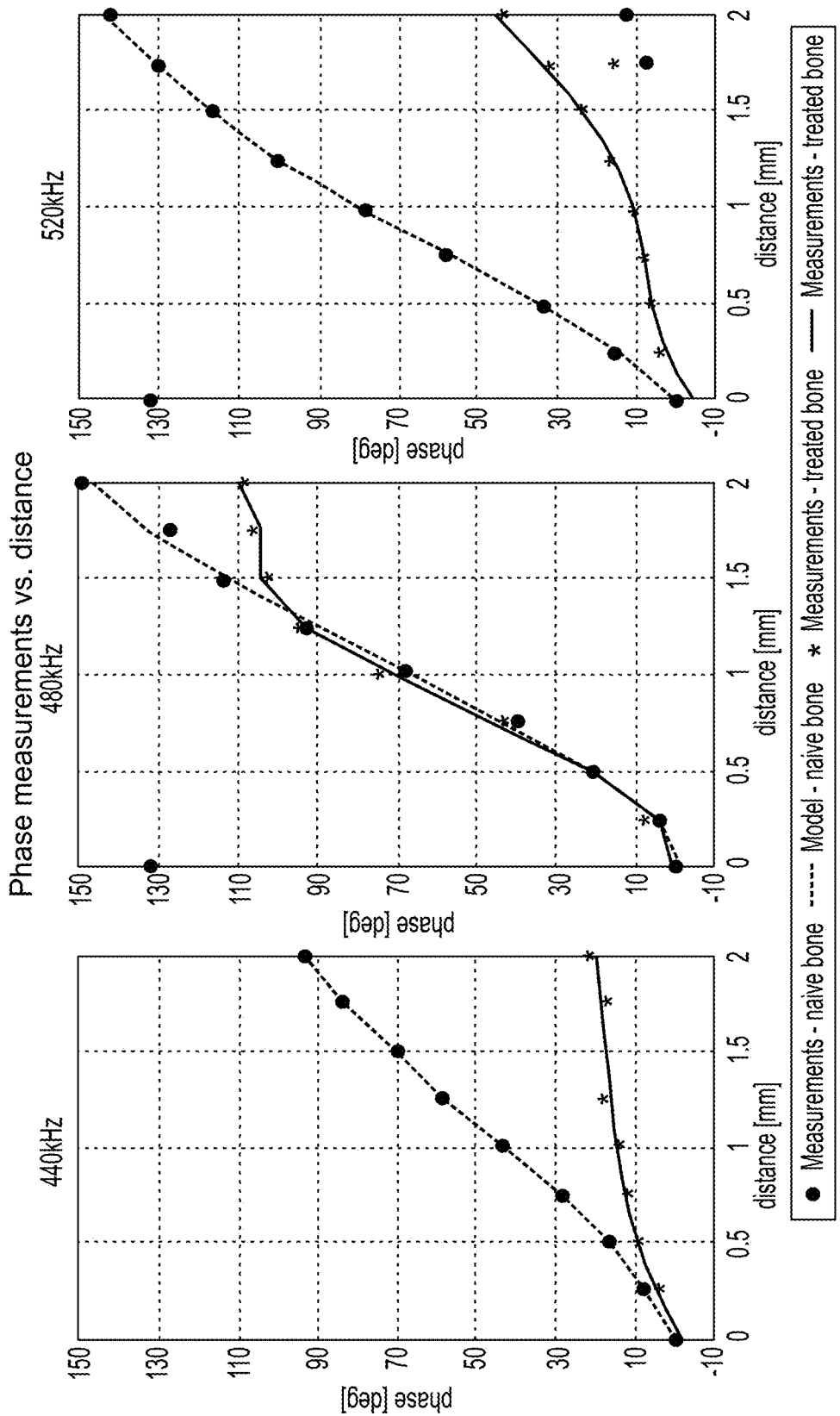

Reference is now made to FIG. 6, which is a series of graphs that describe the measured phases from fowl bone before and after acid treatment. The graphs show measurements of the phase and speed of sound in naïve and dematerialized bone for frequencies of 440 kHz, 480 kHz and 520 kHz respectively.

In the graphs, blue dots represent measurements of the naive bone, and the green line represents the model of naive bone. Black asterisks represent measurements on treated bone and the red lines represent the model of treated bone.

All plots were made after the subtraction of the electromagnetic interference as described in equation 1. Phases are plotted as a function of the distance from the transducer in dots for naïve bone or asterisks for dematerialized bone for each ultrasonic frequency. Also plotted are the fitted phases using equation 2. It is clear that the at least two different ultrasonic modes with different phases are present as the measured phases deviate considerably from linear phase accumulation. It is also evident that the two phasors model explains the measurement quite accurately. This correlates well with theoretical models of guided waves in bone such as that presented by Zhou et al—Ta, D., Wang, W., Wang, Y. Y., Le, L. H. & Zhou, Y. Measurement of the dispersion and attenuation of cylindrical ultrasonic guided waves in long bone. *Ultrasound in medicine & biology* 35, 641-652 (2009)—which predicts the existence of only two guided modes for 0.5 MHz and 1 mm cortical thickness.

Estimated by equation 2, the speed of sound for naïve bone was between 750 m/s up to 900 m/s for the slow wave and was 2500 m/s-3500 m/s for the fast wave. For the dematerialized bone, results varied greatly. Slow wave speeds were estimated in a wide spectrum around 1500 m/s and fast wave estimated speeds varied around 4200 m/s. The great variability in measurements can be explained by both numerical inaccuracies due to the fitting of a complicated model as well as the extreme dispersion (up to hundreds of m/s per 100 KHz) predicted by theoretical models in the frequency/cortical thickness regime.

Finally, the ratio between the slow and fast mode generation efficiency $A_{fs}$ was also estimated by equation 2. This ratio was estimated to be in the range of 8 to 10 for naive bone, while dematerialized bone exhibited significantly lower values of 2 to 4. Thus, dematerialized bones allow for the generation of both modes on a more equal footing.

Figure 7:
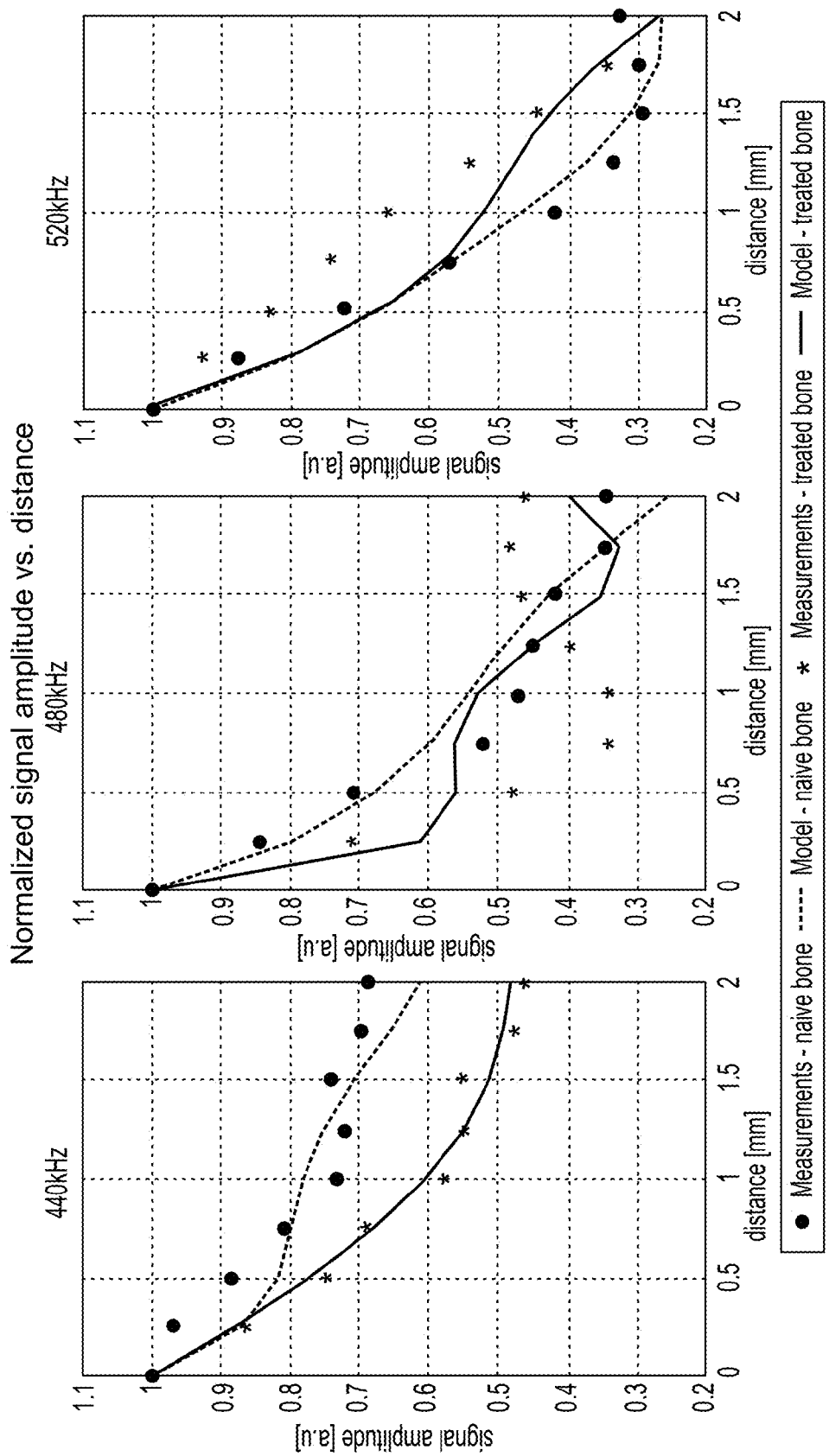

Reference is now made to FIG. 7, which is a series of three graphs of normalized signal amplitude v distance showing ultrasonic attenuation in naïve and dematerialized bone for different frequencies. Again, the frequencies of 440, 480 and 520 kHz are taken, and dots or asterisks indicate measurements and lines indicate the models.

The amplitudes of the ultrasonic signal were analyzed using equation 3. Here the fitting quality was not as good as for the phase measurements. Although the exponential decay in signal amplitudes is clearly seen, inhomogeneities in the bone absorption along its axis render this measurement quite noisy. Ultrasonic attenuations estimated using the model were high—around 30 dB/(cm·Mhz) for naive bones and around 40 dB/(cm·Mhz) for dematerialized bones.

Reference is now made to FIG. 8, which is a simplified diagram showing photoacoustic generation efficiency spectrum measured on cortical bone sample.

In FIG. 8, results of the multispectral photoacoustic excitation of a rat tibia are shown on the left in asterisks. On the right, for comparison, presented are the absorption spectra of several other tissue chromophores such as oxy and deoxy-hemoglobin (shown in red and purple respectively), water (blue) and fat (orange). The PA generation spectrum was decomposed into a sum of these four chromophores and the relative weights were found to best fit the measured spectrum. The fitted spectrum was composed of roughly 40% oxy-hemoglobin, 45% deoxy-hemoglobin, less than 1% fat and about 14% water. It can be seen that most of the bone PA spectrum originates from the deoxygenated blood in the bone marrow. De-oxygenation occurs due to the relatively long time (a few days) from the extraction of the bone to the measurement. The low fat content is attributed to the removal of all soft tissue and to the young age of the rat, and the bone marrow was not fatty. The spectrum is similar to the optical absorption spectrum obtained by Pifferi, A. et al.—Optical biopsy of bone tissue: a step toward the diagnosis of bone pathologies. *Journal of Biomedical Optics*, 474 (2004)—for whole calcaneus bone in-vivo for women in different ages. However, it should be noted that Pifferi measured the soft tissue as well and thus large amounts of oxygenated hemoglobin and fat were present as well.

Reference is now made to FIG. 9, which illustrates a variation of the experimental apparatus of FIG. 4 using multiple single wavelength laser sources.

As with FIG. 4, the arrangement consists of a specialized acoustic bath 200 which was filled with phosphate buffered saline solution of pH 7.2 (Sigma-Aldrich P5493). The bath inner walls were covered with a reflective surface to prevent the generation of PA signals due to light absorption by the bath. The bath has two compartments 202, 204, separated by a removal barrier 206, for excitation and detection of the PA signal in the bone. The bone 208 which passes through a small hole in the barrier, guides waves from one compartment to the outer. Such separation prevents any stray light reflected from the bone surface, say due to small surface irregularities, from reaching the transducer generating an acoustic signal which did not propagate inside the bone shaft. A computer controlled arbitrary waveform generator 210 (Agilent Technologies, 33522B) was used for analog direct modulation of the intensity of triple, fiber coupled laser diodes 212 (Omicron Laserage, BrikxX series). The wavelengths and peak powers of the diode lasers were 650 nm, 760 nm and 1064 nm with peak powers of 0.6 W, 1.2 W and 1.3 W respectively. The modulation was sinusoidal with a frequency of 500 kHz. The outputs of the laser diodes were interchangeably coupled into a multimode fiber 214 (200 μm core step-index fiber, N.A 0.22). The fiber output was collimated with an adjustable focus fiber collimator 216 (Thorlabs, CFC-5X-B) and the incident beam location on the distal end of the bone sample was scanned using computer controlled 50 mm travel motorized translation stage 218 (Thorlabs, MTS50-Z8E). At each experiment, the location of the beam was scanned along the bone over a 20 mm distance with 0.5 mm intervals. A 0.5 MHz, ultrasonic immersion transducer 220 (The Ultran Group, GS500-D13) was used to measure the ultrasonic waves in the proximal end of the bone. The received signals were amplified by preamplifier (Olympus, 5660B, 40 dB gain V/V) followed by a low noise amplifier 222 (Stanford Research Systems, SR560, 60 dB gain V/V) and measured by a computer controlled RF spectrum analyzer 224 (Agilent Technologies, PXA-N9030A with the VSA 89061B program). Such an analyzer may have Vector Signal Analysis capabilities, which enable measurement of both the amplitude and phase at each frequency.

In use, the AWG 210 intensity modulates the diode laser output. The laser is fiber coupled and guided via collimator to the bone sample. The excitation location is scanned over the bone axis using a motorized stage. Guided acoustic modes are generated inside the bone in the excitation compartment 202 and travel through the bone to the detection compartment 204. The PA signal is picked up by the transducer 220, amplified and measured by Vector Signal Analyzer 224. All parts of the setup may be computer controlled.

Reference is now made to FIGS. 10A-C, which are simplified graphs illustrating separate amplitude and phase plots against models for an embodiment of the present invention. Table 1 shows an analysis of the measurements.

TABLE 1 analysis of measurements in FIGS. 10A-C.

| | Measurement 1 | Measurement 2 | Measurement 3 | Mean | Standard Deviation | Relative Error |
|---|---|---|---|---|---|---|
| $C_{fast}$ [m/s] | 4344 | 4329 | 4382 | 4352 | 27.32 | 0.63% |
| $C_{slow}$ [m/s] | 2575 | 2559 | 2581 | 2572 | 11.37 | 0.44% |
| $A_{fs}$ [#] | 1.350 | 1.342 | 1.367 | 1.353 | 0.013 | 0.94% |

Table 1—analysis of measurements in FIGS. 10A-C.

FIGS. 10A-C illustrate system repeatability tests on a single bone at 650 nm excitation wavelength. In (a) three consecutive amplitude traces (full lines) are shown. In (b) their counterpart phase traces (same lines) and a two phasor model fitting (stars) are shown. In (c) an illustration is shown of the fitted phasors. In the phasor diagrams, the red arrow indicates fast mode, the blue arrow indicates the slow propagation mode, and the purple arrow indicates their combination or resultant.

FIGS. 11a-d are simplified graphs showing amplitude and phase plots for different wavelength according to embodiments of the present invention from which a BMD may be calculated. The graphs show PA measurements at different wavelengths. In (a) amplitude traces of three excitation wavelengths are shown for the $1^{st}$ bone sample—650 nm (gold and purple lines), 760 nm (red and cyan lines) and 1064 nm (blue line), (b) shows their counterpart phase traces as full lines with the same color code. (c) shows amplitude traces of three wavelengths from the $2^{nd}$ bone sample—650 nm (gold and purple lines), 760 nm (red and cyan lines) and 1064 nm (blue and green lines), and (d) shows their counterpart phase traces (full lines with the same color code).

FIGS. 12a-d are simplified graphs showing amplitude and phase plots for different wavelengths before and after an induced osteoporotic process and showing the change in waveform due to the osteoporosis. PA measurements are shown at 650 nm before and after induced osteoporosis by EDTA treatment. (a) shows amplitude traces from the $1^{st}$ bone sample before EDTA (gold, purple and cyan lines), and after 20 hours of EDTA treatment (blue and green lines), (b)

shows amplitude traces from the 2$^{nd}$ bone sample before EDTA (gold, purple and cyan lines), and after the same EDTA treatment (blue, red and green lines), (d) shows their counterpart phase traces (full lines with the same color code).

CONCLUSIONS

Frequency domain photoacoustic measurements of bone parameters were demonstrated over multiple acoustic and optical frequencies. The measurements of phase and amplitude of the photoacoustic signal in the modulation frequency may reveal the existence of fast and slow modes which propagate in the bone. The speed of each mode and their relative amplitude convey biomechanical information regarding the bone strength. Though some of the measurements are still noisy and require further research to be interrupted and processed correctly, it was shown that such a method has the potential to provide important information regarding the bone status. Amplitude measurements over the bone axis were greatly affected by bone absorption inhomogeneities. In addition, it was shown that the measurement of PA generation in multiple wavelengths can be used to obtain information about the bone chemical content. These results suggest that a complete characterization of the bone over a region of both acoustic and spectral frequencies can be used as a powerful tool for in-vivo bone evaluation.

The terms "comprises", "comprising", "includes", "including", "having" and their conjugates mean "including but not limited to".

The term "consisting of" means "including and limited to".

As used herein, the singular form "a", "an" and "the" include plural references unless the context clearly dictates otherwise.

It is appreciated that certain features of the invention, which are, for clarity, described in the context of separate embodiments, may also be provided in combination in a single embodiment, and the above description is to be construed as if this combination were explicitly written. Conversely, various features of the invention, which are, for brevity, described in the context of a single embodiment, may also be provided separately or in any suitable subcombination or as suitable in any other described embodiment of the invention, and the above description is to be construed as if these separate embodiments were explicitly written. Certain features described in the context of various embodiments are not to be considered essential features of those embodiments, unless the embodiment is inoperative without those elements.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

What is claimed is:

1. An apparatus for examining bone in vivo, comprising:
a laser source configured to produce a laser beam;
an acousto-optic modulator, configured to modulate said laser beam at acoustic frequencies being frequencies that are able to give rise to acoustic waves;
a waveform generator configured to drive said acousto-optic modulator with a modulation signal at a range of said acoustic frequencies, thereby to produce a modulated multiple frequency acousto-optic beam able to cause excitation at a plurality of frequencies;
a spectrum analyzer, configured to analyze received signals from said bone, said received signals including signals resulting from acoustic waves traveling within said bone caused by said modulated multiple frequency acousto-optic beam, wherein said spectrum analyzer is further configured to analyze said received signals of said modulated multiple frequency acousto-optic beam at optical wavelengths and acoustic frequencies, and to scan said optical wavelengths and acoustic frequencies to map a bone transfer function, and further to analyze amplitude and phase with variation of said frequency to determine a speed of sound dispersion and a broadband ultrasonic attenuation, said spectrum analyzer being further configured to determine a mineral density and a bone quality for said bone from said analyzing.

2. The apparatus according to claim 1, wherein said spectrum analyzer is further configured to use said bone transfer function, said speed of sound dispersion and said broadband ultrasonic attenuation to determine biochemical composition of said bone.

3. The apparatus according to claim 1, further comprising a beam director to direct said laser beam towards said bone at an excitation point separated from a measurement point, such that acoustic waves enter said bone substantially at said excitation point and travel down said bone to said measurement point.

4. The apparatus according to claim 3, further comprising an ultrasonic transducer located on said limb at said measurement point to measure ultrasonic wave propagation at said measurement point.

5. The apparatus according to claim 1, wherein said waveform generator is configured to select a frequency to define said frequency range for said photoacoustic signals, the selected frequency being at or above half a megahertz.

6. An apparatus for examining bone in vivo, comprising:
a laser source configured to produce a laser beam;
an acousto-optic modulator, configured to modulate said laser beam at acoustic frequencies being frequencies that are able to give rise to acoustic waves;
a waveform generator configured to drive said acousto-optic modulator with a modulation signal at a range of said acoustic frequencies, thereby to produce a modulated multiple frequency acousto-optic beam able to cause excitation at a plurality of frequencies;
a spectrum analyzer, configured to analyze received signals from said bone, said received signals including signals resulting from acoustic waves traveling within said bone caused by said modulated multiple frequency acousto-optic beam, said spectrum analyzer being further configured to determine a mineral density and a bone quality for said bone, said spectrum analyzer further configured to obtain a measurement of quantitative ultrasound (QUS) parameters of the bone and a measurement of a near infra-red (NIR) absorption spectrum of the bone.

7. A method for examining bone in vivo, comprising:
using a laser to provide a laser beam;
modulating said laser beam using an acoustic signal, thereby to produce a laser beam at frequencies being able to give rise to acoustic waves within said bone;
directing said modulated beam at a bone to cause acoustic waves caused by said beam to travel through said bone at a plurality of frequencies;
analyzing received signals from said bone, said received signals including signals resulting from said acoustic waves traveling within said bone, wherein said analyzing comprises scanning optical wavelengths and acoustic frequencies, and further analyzing amplitude and phase as acoustic frequency varies to determine a speed of sound dispersion and a broadband ultrasonic attenuation;
using results of said scanning of optical wavelengths and acoustic frequencies to map a bone transfer function; and
determining a mineral density and a bone quality for said bone.

8. The method according to claim 7, further comprising using said bone transfer function, said speed of sound dispersion and said broadband ultrasonic attenuation to determine biochemical composition of said bone.

9. The method according to claim 7, wherein said directing said laser beam is to cause acoustic waves generated by said laser beam to travel through said bone substantially from a predetermined excitation point separated from a measurement point, such that said acoustic waves travel down said bone to said measurement point, the method further comprising measuring said acoustic waves at said measurement point.

10. The method according to claim 7, comprising selecting a frequency to define a range for said acoustic waves, the selected frequency being at or above half a megahertz.

11. Method A method for examining bone in vivo, comprising:
using a laser to provide a laser beam;
modulating said laser beam using an acoustic signal, thereby to produce a laser beam at frequencies being able to give rise to acoustic waves within said bone;
directing said modulated beam at a bone to cause acoustic waves caused by said beam to travel through said bone at a plurality of frequencies;
gathering signals from said bone; and
analyzing received signals from said bone, said received signals including signals resulting from said acoustic waves traveling within said bone, wherein said analyzing obtains a measurement of quantitative ultrasound (QUS) parameters of the bone and a measurement of a near infra-red (NIR) absorption spectrum of the bone.

* * * * *